(12) United States Patent
Tsymbalenko

(10) Patent No.: US 9,420,996 B2
(45) Date of Patent: Aug. 23, 2016

(54) METHODS AND SYSTEMS FOR DISPLAY OF SHEAR-WAVE ELASTOGRAPHY AND STRAIN ELASTOGRAPHY IMAGES

(71) Applicant: General Electric Company, Schenectady, NY (US)

(72) Inventor: Yelena Viktorovna Tsymbalenko, Mequon, WI (US)

(73) Assignee: General Electric Company, Schenectady, NY (US)

( * ) Notice: Subject to any disclaimer, the term of this patent is extended or adjusted under 35 U.S.C. 154(b) by 66 days.

(21) Appl. No.: 14/168,559

(22) Filed: Jan. 30, 2014

(65) Prior Publication Data

US 2015/0209013 A1 Jul. 30, 2015

(51) Int. Cl.
| | |
|---|---|
| *A61B 8/00* | (2006.01) |
| *A61B 8/08* | (2006.01) |
| *G01S 7/52* | (2006.01) |
| *G01S 15/89* | (2006.01) |

(52) U.S. Cl.
CPC ............ *A61B 8/485* (2013.01); *A61B 8/463* (2013.01); *A61B 8/467* (2013.01); *A61B 8/483* (2013.01); *A61B 8/5207* (2013.01); *G01S 7/52022* (2013.01); *G01S 7/52042* (2013.01); *G01S 7/52071* (2013.01); *G01S 7/52074* (2013.01); *G01S 7/52084* (2013.01); *G01S 15/8993* (2013.01); *A61B 8/4254* (2013.01); *A61B 8/4405* (2013.01); *A61B 8/4427* (2013.01); *A61B 8/466* (2013.01); *A61B 8/469* (2013.01); *G01S 15/899* (2013.01)

(58) Field of Classification Search
CPC .................................. A61B 8/00; A61N 7/00
USPC ......................................................... 600/400
See application file for complete search history.

(56) References Cited

U.S. PATENT DOCUMENTS

| | | | |
|---|---|---|---|
| 2009/0163805 A1 | 6/2009 | Sunagawa et al. | |
| 2010/0016718 A1 | 1/2010 | Fan et al. | |
| 2010/0256530 A1 | 10/2010 | Varghese et al. | |
| 2010/0286520 A1 * | 11/2010 | Hazard et al. ................ | 600/439 |
| 2011/0152687 A1 | 6/2011 | Iimura et al. | |
| 2011/0237945 A1 | 9/2011 | Foroughi et al. | |

(Continued)

OTHER PUBLICATIONS

"Characterizing expansion and stiffening of the canine liver with increasing hepatic pressure," Rotemberg et al., 2012 IEEE International Ultrasonics Symposium Proceedings, Oct. 7, 2012, pp. 101-104.

(Continued)

*Primary Examiner* — Joel F Brutus
(74) *Attorney, Agent, or Firm* — Dean D. Small; The Small Patent Law Group, LLC.

(57) ABSTRACT

Methods and systems for displaying ultrasound images are provided. The method provides receiving a user input selecting a shear-wave mode for an ultrasound probe and obtaining shear-wave data of a region of interest (ROI) acquired by the ultrasound probe when in the shear-wave mode. The method further includes receiving a user input selecting a strain mode for the ultrasound probe and obtaining strain data of the ROI acquired by the ultrasound probe when in the strain mode. The method also includes generating an image of the shear-wave data and an image of the strain data and receiving a user input to display the shear-wave image and the strain image. Further, the method provides displaying the shear-wave image and the strain image concurrently.

20 Claims, 9 Drawing Sheets

(56) References Cited

U.S. PATENT DOCUMENTS

| | | | |
|---|---|---|---|
| 2012/0123263 A1* | 5/2012 | Osaka et al. | 600/438 |
| 2012/0136250 A1* | 5/2012 | Tabaru et al. | 600/438 |
| 2013/0096430 A1 | 4/2013 | Yoshiara et al. | |
| 2013/0169632 A1 | 7/2013 | Sawayama | |
| 2013/0261453 A1 | 10/2013 | Tamura | |

OTHER PUBLICATIONS

"Monitoring of Thermal Therapy Based on Shear Modulus Changes: II. Shear Wave Imaging of Thermal Lesions," Arnal et al., IEEE Transactions on Ultrasonics, Ferroelectrics and Frequency Control, IEEE, US., vol. 58, No. 8, Aug. 1, 2011, pp. 1603-1611.

* cited by examiner

METHODS AND SYSTEMS FOR DISPLAY OF SHEAR-WAVE ELASTOGRAPHY AND STRAIN ELASTOGRAPHY IMAGES

BACKGROUND OF THE INVENTION

Embodiments described herein generally relate to ultrasound imaging systems, and more particularly to displaying information using ultrasound imaging systems, such as shear-wave elastography images and strain elastography images.

Ultrasound elasticity imaging is an elastography imaging modality that employs ultrasound waves to probe the mechanical properties of biological tissues and produce corresponding images. Ultrasound elasticity imaging can be subdivided into two types: strain elastography imaging (SEI) and shear-wave elastography imaging (SWEI), each having different advantages. For example, SEI has a higher sensitivity than SWEI, however, SWEI has a higher specificity than SEI.

SEI is a qualitative technique based on measuring differences in compression displacement of the tissue by applying deformation or compression to a region of interest from an external or patient source. Changes in tissue stiffness, such as an organ, may be an indicator of disease. Accordingly, measuring tissue stiffness allows a physician to identify or detect liver fibrosis and cirrhosis, prostate cancer, breast cancer, and the like. For example, a portion of the tissue may be stiffer than surrounding tissues indicating an onset or presence of a disease such as cancer, tumor, fibrosis, steatosis, or other such conditions.

SWEI is based on applying acoustically generated shear-waves to determine mechanical properties of the tissue, usually measured as a velocity, by tracking the displacement of the tissue at a plurality of points caused by the shear-wave over time. The velocity relates to one or more mechanical properties of the tissue and may provide stiffness information measured in, for example, kilo Pascals (kPa). For example, a normal glandular measured from a patient is approximately 57 kPa, alternatively, a ductal tumor or breast cancer is approximately 301 kPa.

Ultrasound imaging systems are known that can display different ultrasound images. However, these known systems cannot display SEI and SWEI frame images concurrently or as an overlay of SEI on top of SWEU or vice versa. Further, these systems are not able to concurrently display the SEI images while acquiring the SWEI image frames (or vice versa) concurrently. Due to the different information provided by and the differing advantages of SEI and SWEI, a need exists for an ultrasound imaging system able to display the SEI and SWEI images concurrently.

BRIEF DESCRIPTION OF THE INVENTION

In an embodiment, a dual mode ultrasound imaging system is provided that includes an ultrasound probe configured to acquire shear-wave data and strain data for a region of interest (ROI). The system further includes a diagnostic circuit configured to generate a shear-wave image and a strain image from the shear-wave data and the strain data, respectively. Further, the system includes a display concurrently displaying the shear-wave image and the strain image.

In another embodiment, a method for displaying ultrasound images is provided. The method provides receiving an input selecting a shear-wave mode for an ultrasound probe and obtaining shear-wave data of a region of interest (ROI) acquired by the ultrasound probe when in the shear-wave mode. The method further includes generating shear-wave images from the shear-wave data and display the shear-wave images on a display. The method also includes receiving a user input selecting a compare mode and switching to a side-by-side display mode such that at least one of the shear-wave images is displayed on a first screen portion of the display. The method provides, further, receiving an input selecting a strain mode for the ultrasound probe, obtaining strain data of the ROI acquired by the ultrasound probe when in the strain mode, and generating shear-wave images from the shear-wave data. Further, the method provides displaying the strain images on a second screen portion of the display concurrently with the at least one of the shear-wave images.

In another embodiment, a method for displaying dual mode ultrasound images on a display is provided. The method provides receiving user inputs from a user input device having user selectable element to control a display. The user inputs control the display to enter into a side-by-side display more or an overlay display mode. The method further provides defining, while the display is in the side-by-side display mode, a first screen portion to display a strain image and a second screen portion to display a shear-wave image, respectively, such that the strain image and the shear-wave image are displayed concurrently. Further, the method provides overlaying, while the display is in the overlay display mode, the strain image and the shear-wave image to form a single image. The single image is aligned using region of interest (ROI) data acquisition locations of the strain image and the shear-wave image.

DETAILED DESCRIPTION OF THE INVENTION

Figure 1:
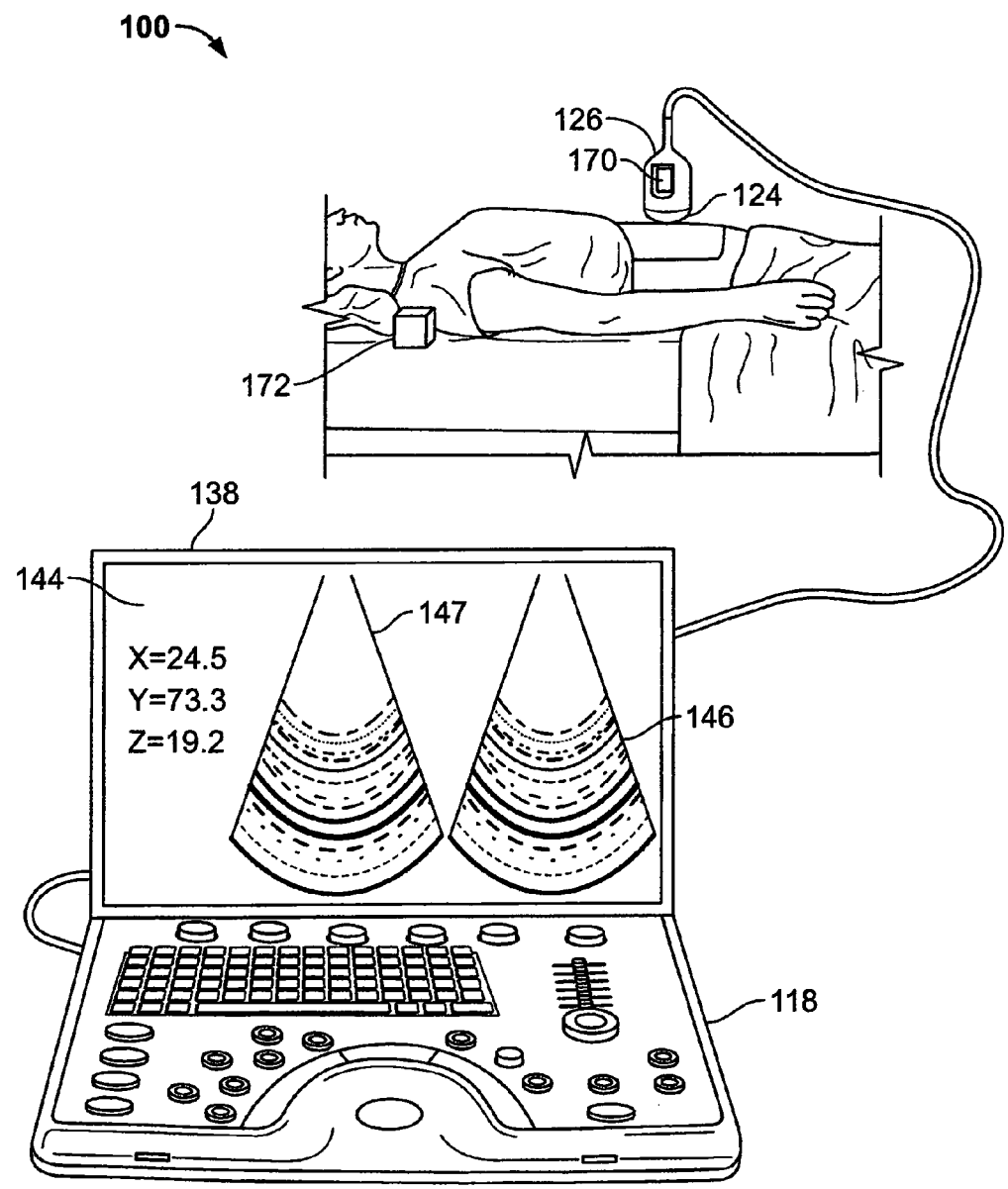
FIG. 1 is an illustration of an ultrasound imaging system in accordance with an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry or software. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

At least one technical effect of various embodiments is increased accuracy in characterizing the mechanical properties of imaged tissue.

FIG. 1 illustrates an ultrasound imaging system 100 formed in accordance with various embodiments in which images generated from shear-wave elastography imaging (SWEI) and strain elastography imaging (SEI) may be concurrently displayed. For example, the system 100 may include a portable computer 118 (or other computing device, such as a workstation) having a display 138 for displaying the images.

The system 100 generally includes an ultrasound probe 126 that is coupled to the computer 118. The probe 126 may include a probe position device 170. Further, the system 100 may also include a reference position device 172 that may be located near the patient or may be attached to the patient. The position devices 170 and 172 may have transmitters and/or receivers that communicate with each other and/or with the computer 118. For example, the position devices 170 and 172 may communicate with a position tracking circuit 148 (shown in FIG. 2). The position tracking circuit 148 may receive signals from the position devices 170 and 172. In one particular embodiment, the position device 172 has a pair of coils that create an electromagnetic field. The position tracking circuit 148 receives data (e.g., positional information) from the position devices 170 and 172 regarding a location of the probe 126. As the probe 126 acquires measurements of the patient, the display 138 may show a ROI data acquisition location 144 illustrated as a three dimensional coordinate. The location 144 represents the location of the probe 126, with respect to the patient, when acquiring ultrasound data of the ROI. Alternatively, the location 144 represents the location of the probe 126 with respect to the ROI relative to a reference point, such as a mechanical structure of the ROI, designated by a user (e.g., doctor or operator).

Figure 2:
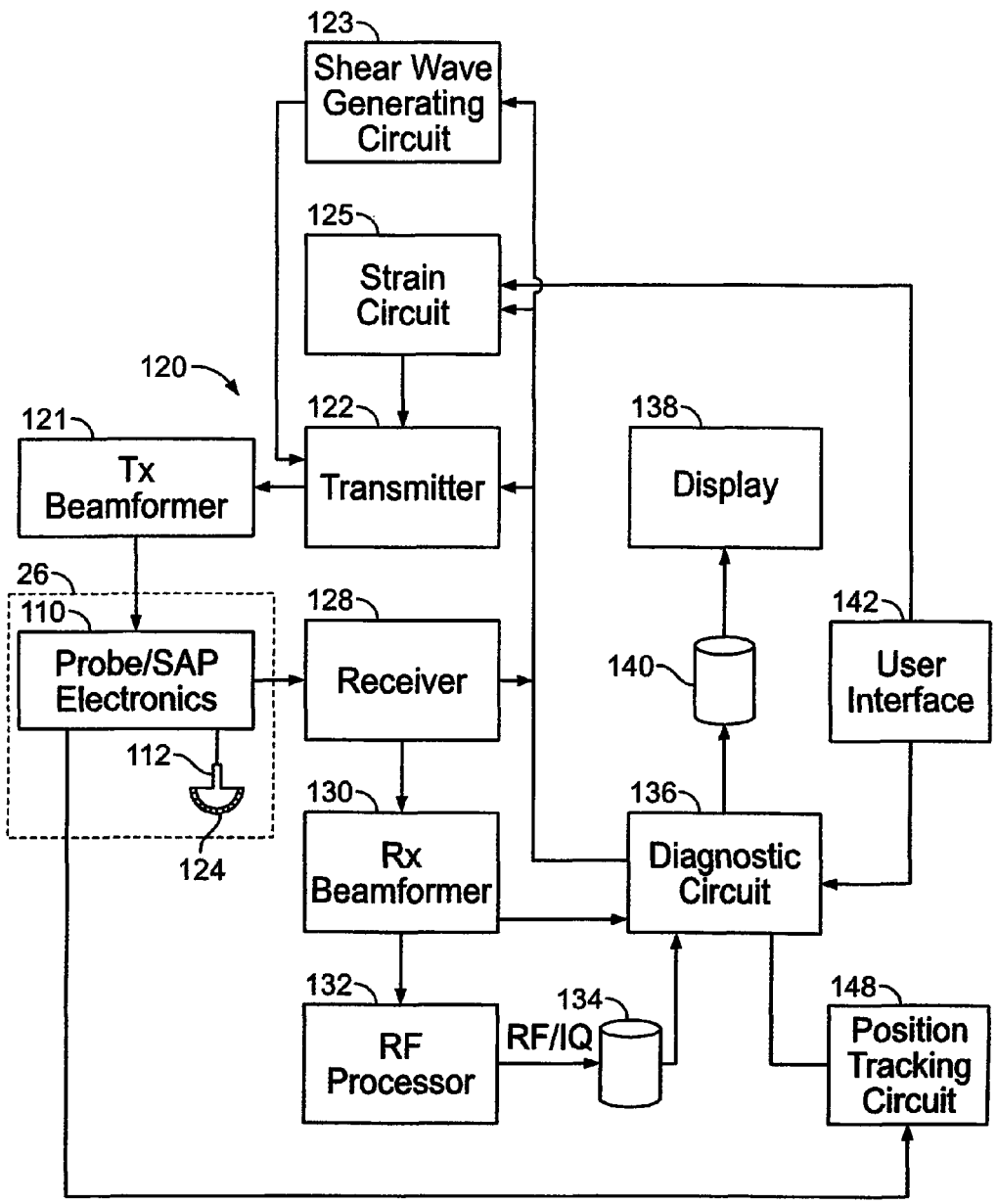
FIG. 2 is an illustration of simplified block diagram of an ultrasound imaging system in accordance with an embodiment.

FIG. 2 is a simplified block diagram of an ultrasound system 120 that may be embodied as the ultrasound imaging system 100. In the illustrated embodiment, the ultrasound system 120 includes the probe 126 having a transmitter 122 and probe/SAP electronics 110. The transmitter 122 transmits a signal to a transmit beamformer 121 which in turn drives the transducer elements 124 within the transducer array 112. The transducer elements 124 emit pulsed ultrasonic signals into the patient. A variety of a geometries and configurations may be used for the array 112. Further, the array 112 of transducer elements 124 may be provided as part of, for example, different types of ultrasound probes.

The transducer elements 124, for example piezoelectric crystals, emit pulsed ultrasonic signals into a body (e.g., patient) or volume. The ultrasonic signals may include, for example, one or more reference pulses, one or more pushing pulses (e.g., shear-waves), and/or one or more tracking pulses. At least a portion of the pulsed ultrasonic signals back-scatter from a region of interest (ROI) (e.g., breast tissues, liver tissues, cardiac tissues, prostate tissues, and the like) to produce echoes. The echoes are delayed in time according to a depth, and are received by the transducer elements 124 within the transducer array 112. The ultrasonic signals may be used for imaging, for generating and/or tracking shear-waves, for measuring differences in compression displacement of the tissue (e.g., strain), and/or for therapy, among other uses. For example, the probe 126 may deliver low energy pulses during imaging and tracking, medium to high energy pulses to generate shear-waves, and high energy pulses during therapy.

The transducer array 112 may have a variety of array geometries and configurations for the transducer elements 124 which may be provided as part of, for example, different types of ultrasound probes. The probe/SAP electronics 110 may be used to control the switching of the transducer elements 124. The probe/SAP electronics 110 may also be used to group the transducer elements 124 into one or more sub-apertures.

The transducer elements 124 convert the received echo signals into electrical signals which may be received by a receiver 128. The electrical signals representing the received echoes are passed through a receive beamformer 130, which performs beamforming on the received echoes and outputs an RF signal. The RF signal is then provided to an RF processor 132 that processes the RF signal. Alternatively, the RF processor 132 may include a complex demodulator (not shown) that demodulates the RF signal to form IQ data pairs representative of the echo signals. The RF or IQ signal data may then be provided directly to a memory 134 for storage (e.g., temporary storage). Optionally, the output of the beamformer 130 may be passed directly to a diagnostic circuit 136.

The ultrasound system 120 also includes a processor or the diagnostic circuit 136 to process the acquired ultrasound information (e.g., RF signal data or IQ data pairs) and prepare frames of ultrasound information for display on the display 138. The diagnostic circuit 136 may include one or more separate processing components. For example, the diagnostic circuit 136 may include a central processing unit (CPU), a microprocessor, a graphics processing unit (GPU), or any other electronic component capable of processing inputted data according to specific logical instructions. Having the diagnostic circuit 136 that includes a GPU may be advantageous for computation-intensive operations, such as volume-rendering.

The diagnostic circuit 136 is adapted to perform one or more processing operations according to a plurality of selectable ultrasound modalities on the acquired ultrasound information. Acquired ultrasound information may be processed in real-time during a scanning or therapy session as the echo signals are received. Additionally or alternatively, the ultrasound information may be stored temporarily in the memory 134 during a scanning session and processed in less than real-time in a live or off-line operation. An image memory 140 is included for storing processed frames of acquired ultrasound information that are not scheduled to be displayed immediately or to store post-processed images (e.g., shear-wave images, strain images). The image memory 140 may comprise any known data storage medium, for example, a permanent storage medium, removable storage medium, etc.

The position tracking circuit 148 tracks a position of the probe 126 and communicates the position to the diagnostic circuit 136 as described above. Optionally, the diagnostic circuit 136 may associate or correlate the ROI data acquisition location of the probe 126 with the acquisition of data corresponding to the SEI and/or SWEI, respectively, in the image memory 140.

The diagnostic circuit 136 is connected to a user interface 142 that controls operation of the diagnostic circuit 136 and the display 138 as explained below in more detail and is configured to receive inputs from the user, for example a keyboard, a keypad, buttons, a touchscreen. The display 138 may include one or more monitors that present patient information, including diagnostic and therapeutic ultrasound images to the user for review, diagnosis, analysis, and treatment. The display 138 may automatically display, for example, one or more 2D, 3D, or 4D ultrasound data sets stored in the memory 134 or 140 or currently being acquired. One or both of the memory 134 and the memory 140 may store 3D data sets of the ultrasound data (e.g., shear-wave data, strain data), where such 3D data sets are accessed to present 2D and 3D images. For example, a 3D ultrasound data set may be mapped into the corresponding memory 134 or 140, as well as one or more reference planes. The processing of the data, including the data sets, may be based in part on user inputs, for example, user selections received at the user interface 142.

The diagnostic circuit 136 is configured to analyze ultrasound signals to obtain the SEI and/or SWEI of the ROI. Furthermore, the diagnostic circuit 136 may also automatically differentiate tissue of the ROI from non-ROI tissue. The diagnostic circuit 136 may also be configured to receive user imaging commands for highlighting or outlining the image, a display layout (e.g., side-by-side, overlaid), or otherwise providing an overlay that indicates the ROI within the SEI and/or SWEI.

The diagnostic circuit 136 may be configured to control the probe 126 by having the probe 126 enter into diagnostic or imaging modes such as a shear-wave mode or a strain mode. For example, the diagnostic circuit 136 may control the probe 126 to enter the shear-wave mode. Once the probe 126 is in the shear-wave mode, the probe 126 may be controlled to deliver a pushing pulse to generate a shear-wave within the ROI automatically within a predetermined time frame or by the user using the user interface 142.

In operation, the system 120 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, etc.). The data may be acquired by moving the probe 126, such as along a linear or curvilinear path, while scanning the ROI. At each linear or arcuate position, the probe 126 obtains scan planes that are stored in the memory 134.

The system 120 includes a shear-wave-generating circuit 123 that is operatively coupled to the diagnostic circuit 136 or a sub-circuit of the diagnostic circuit 136. The shear-wave generating circuit 123 is configured to control the probe 126 when the probe 126 is operated in a shear-wave mode. While in the shear-wave mode, the shear-wave generating circuit 123 may control the probe 126 to generate a shear wave at a site within the ROI of the patient. The shear-wave-generating circuit 123 may control the probe 126 or, more particularly, the transducer elements 124 to direct a shear-wave generating or pushing pulse(s) toward the predetermined site to generate the shear-wave. Alternatively, the shear-wave generating circuit 123 may control another device capable of generating shear-waves having the probe 126 measure or track the velocity as the shear-wave passes through the ROI. For example, the shear-wave-generating circuit 123 may control a therapy transducer, a mechanical actuator, or an audio device to generate the shear waves.

The system 120 also includes a strain circuit 125 that is operatively coupled to the diagnostic circuit 136 or a sub-circuit of the diagnostic circuit 136. The strain circuit 125 is configured to control the probe 126 when the probe 126 operated in a strain mode. While in the strain mode, the strain circuit 125 may control the probe 126 to generate a mechanical (e.g., surface vibration, freehand or step quasi-static surface displacement, or the like) or radiation force on the patient or ROI to measure the stiffness or strain of the ROI of the patient. Alternatively, the strain circuit 125 may control another device capable of generating a mechanical force on the patient or the ROI. For example, a low frequency mechanical vibrator may be applied to the skin surface and the compression motion induced in the underlying tissue, such as on the ROI, is measured by the probe 126.

Figure 3:
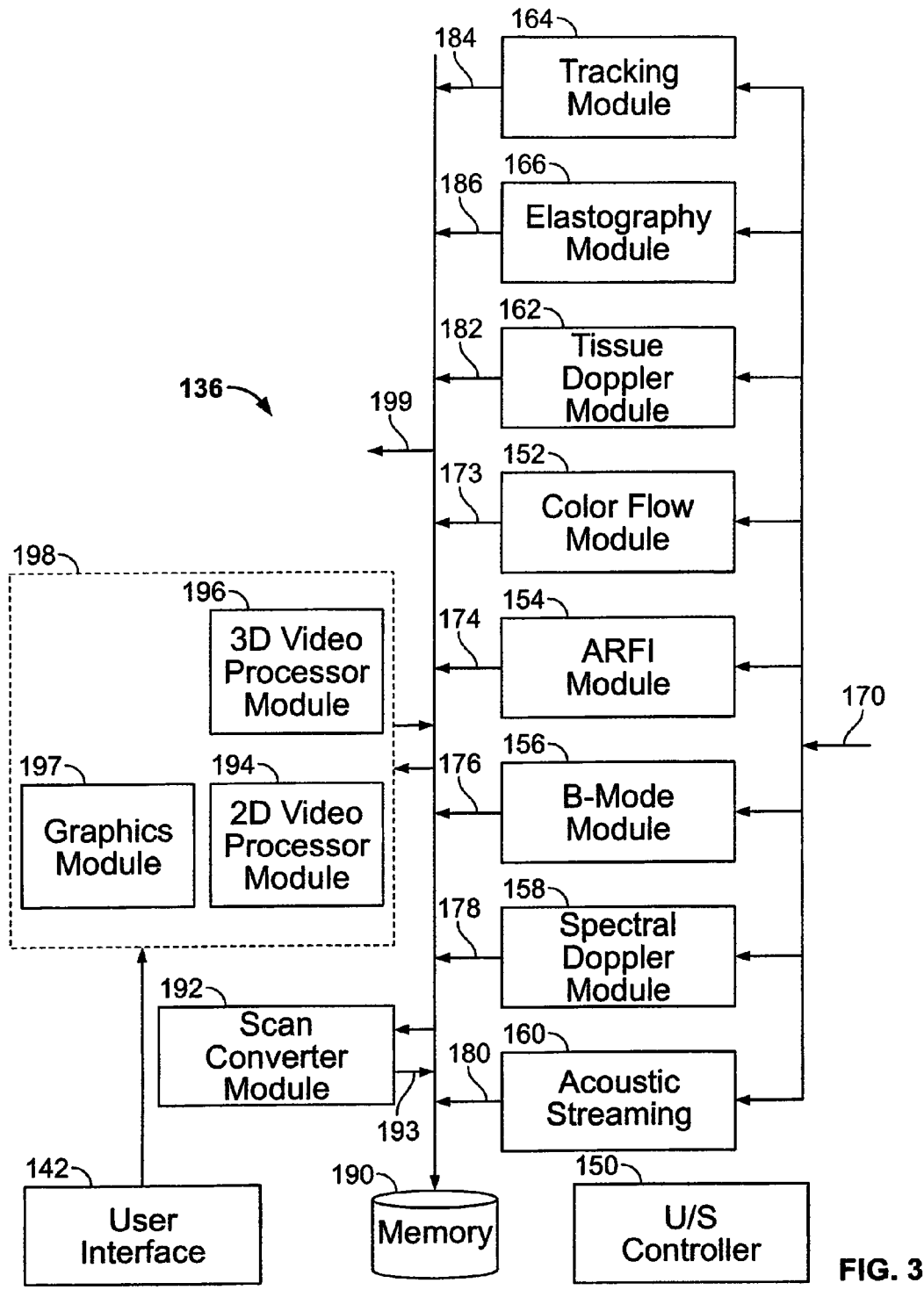
FIG. 3 is an illustration of a simplified block diagram of a diagnostic circuit in the ultrasound imaging system of FIG. 2 in accordance with an embodiment.

FIG. 3 is an exemplary block diagram of the diagnostic circuit 136. The diagnostic circuit 136 (FIG. 3) is illustrated conceptually as a collection of circuits, but may be implemented utilizing any combination of dedicated hardware boards, DSPs, processors, etc. Alternatively, the circuit 136 may be implemented utilizing an off-the-shelf PC with a single processor or multiple processors, with the functional operations distributed between the processors. As a further option, the circuit 136 may be implemented utilizing a hybrid configuration in which certain modular functions are performed utilizing dedicated hardware, while the remaining modular functions are performed utilizing an off-the-shelf PC and the like. The circuit 136 also may be implemented as software circuits within a processing unit.

The operations of the circuit 136 may be controlled by a local ultrasound controller 150 or by the diagnostic circuit 136. The circuits 152-166 perform mid-processor operations. The diagnostic circuit 136 may receive ultrasound data 170 in one of several forms. In the embodiment of FIG. 3, the received ultrasound data 170 constitutes IQ data pairs representing the real and imaginary components associated with each data sample. The IQ data pairs are provided to one or more circuits, for example, a color-flow circuit 152, an acoustic radiation force imaging (ARFI) circuit 154, a B-mode circuit 156, a spectral Doppler circuit 158, an acoustic streaming circuit 160, a tissue Doppler circuit 162, a tracking circuit 164, and an elastography circuit 166. Other circuits may be included, such as an M-mode circuit, power Doppler circuit, among others. However, embodiments described herein are not limited to processing IQ data pairs. For example, processing may be done with RF data and/or using other methods. Furthermore, data may be processed through multiple circuits.

Each of circuits 152-166 is configured to process the IQ data pairs in a corresponding manner to generate, respectively, color-flow data 173, ARFI data 174, B-mode data 176, spectral Doppler data 178, acoustic streaming data 180, tissue Doppler data 182, tracking data 184 (e.g., ROI data acquisition location), elastography data 186 (e.g., strain data, shear-wave data), among others, all of which may be stored in a memory 190 (or memory 134 or image memory 140 shown in FIG. 2) temporarily before subsequent processing. The data 173-186 may be stored, for example, as sets of vector data values, where each set defines an individual ultrasound image frame. The vector data values are generally organized based on the polar coordinate system.

A scan converter circuit 192 accesses and obtains from the memory 190 the vector data values associated with an image frame and converts the set of vector data values to Cartesian coordinates to generate an ultrasound image frame 193 formatted for display. The ultrasound image frames 193 generated by the scan converter circuit 192 may be provided back to the memory 190 for subsequent processing or may be provided to the memory 134 (shown in FIG. 2) or the image memory 140 (FIG. 2). Once the scan converter circuit 192 generates the ultrasound image frames 193 associated with the data, the image frames may be stored in the memory 190 or communicated over a bus 199 to a database (not shown), the memory 134, the image memory 140, and/or to other processors (not shown).

For example, it may be desired to view different ultrasound images relating to a shear-wave therapy session in real-time on the display 138 (shown in FIG. 2). To do so, the scan converter circuit 192 obtains data sets for images stored in the memory 190 of that are currently being acquired from the probe 126 operating in the shear-wave mode. The vector data is interpolated where necessary and converted into an X, Y format for video display to produce SWEI image frames. The scan converted SWEI image frames are provided to a display circuit 198 that may include a video processor that maps the video to a gray-scale mapping for video display. The gray-scale map may represent a transfer function of the raw image data to displayed gray levels. Once the video data is mapped to the gray-scale values, the display controller controls the display 138, which may include one or more monitors or windows of the display, to display the SWEI image frame. The SWEI images displayed in the display 138 is produced from an SWEI frame of data in which each datum indicates the intensity or brightness of a respective pixel in the display.

Referring again to FIG. 3, the display circuit 198 accesses and obtains one or more of the image frames from the memory 190 or from the memory 134 and/or the image memory 140 over the bus 199 to display the images onto the display 138. The display circuit 198 receives user input from the user interface 142 selecting one or image frames to be displayed that are stored on memory (e.g., the memory 190) and/or selecting a display layout or configuration for the image frames.

The display circuit 198 may include a 2D video processor circuit 194. The 2D video processor circuit 194 may be used to combine one or more of the frames generated from the different types of ultrasound information. For example, the 2D video processor circuit 194 may combine different image frames by mapping one type of data to a gray map and mapping the other type of data to a color map for video display. In the final displayed image, the color pixel data is superimposed on the gray scale pixel data to form a single multi-mode image frame that is again re-stored in the memory 190 or communicated over the bus 199. Successive frames of images may be stored as a cine loop (4D images) in the memory 190 or memory 140 (FIG. 2). The cine loop represents a first in, first out circular image buffer to capture image data that is displayed in real-time to the user. The user may freeze the cine loop by entering a freeze command at the user interface 142. The user interface 142 may include, for example, a keyboard and mouse and all other input controls associated with inputting information into the ultrasound system 120 (FIG. 2). In one embodiment, the user interface 142 includes the display 138 that may be touch-sensitive or configured to interact with a stylus. The user interface 142 may also receive user inputs through voice-recognition or activation.

The display circuit 198 may include a 3D processor circuit 196. The 3D processor circuit 196 may access the memory 190 to obtain spatially consecutive groups of ultrasound image frames and to generate three-dimensional image representations thereof, such as through volume rendering or surface rendering algorithms as are known. The three-dimensional images may be generated utilizing various imaging techniques, such as ray-casting, maximum intensity pixel projection and the like.

The display circuit 198 may include a graphic circuit 197. The graphic circuit 197 may access the memory 190 to obtain groups of ultrasound image frames and the ROI data acquisition locations that have been stored or that are currently being acquired. The graphic circuit 197 may generate images that include the images of the ROI and a graphical representation positioned (e.g., overlaid) onto the images of the ROI. The graphical representation may represent an outline of a treatment space, the focal point or region of the therapy beam, a path taken by the focal region within the treatment space, a probe used during the session, the ROI data acquisition location, and the like. Graphical representations may also be used to indicate the progress of the therapy session. The graphical representations may be generated using a saved graphical image or drawing (e.g., computer graphic generated drawing), or the graphical representation may be directly drawn by the user onto the image using a pointing device, e.g., an electronic stylus or mouse, or another interface device.

Figure 4:
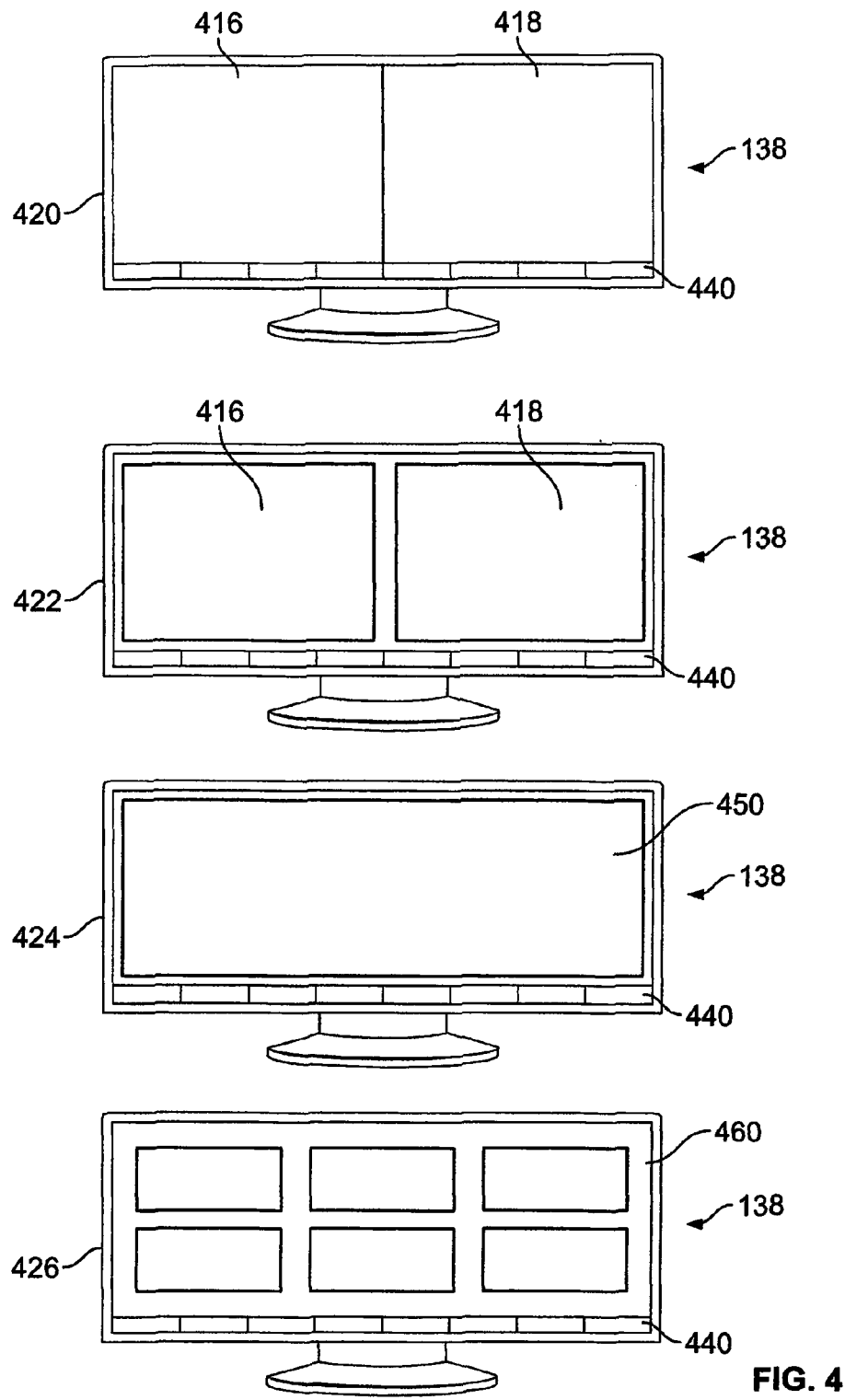
FIG. 4 is an illustration of display layouts of an ultrasound imaging system in accordance with an embodiment.

FIG. 4 illustrates various display layouts, such as side-by-side (e.g., dual display) configurations 420-422, an overlaid configuration 424, and a thumbnail configuration 426 in accordance with various embodiments (and which may be displayed on the display 138). The various display layouts may include labels 440 indicating the display layout being viewed or allow a user to select a different display layout or a different image of the object or ROI displayed. Additionally, the labels 440 may include the ROI acquisition location, such as a Cartesian coordinate, for the images being displayed. The side-by-side configurations 420 and 422 use a side-by-side display technique by dividing the display 138 into a number of sub-screens, such as square or rectangle portions such that each portion includes one image frame. Each portion, illustrated in FIG. 4, includes image frames 416 and 418, respectively. The image frames 416 and 418 may have been acquired from different ultrasound imaging modes, such as shear-wave or strain, that were selected by the user using the user interface 142 or automatically selected by the system 120. The side-by-side configurations 420 and 422 are illustrated having display portions adjacent to one another along a horizontal axis, however, the display portions may be positioned along a vertical axis or diagonally in other embodiments. Additionally or alternatively, the side-by-side configurations 420 and 422 may be divided into more display portions than illustrated in FIG. 4, thus allowing more than two image frames to be displayed.

The overlaid configuration 424 displays a single image, which can be an overlaid image 450 formed from one or more image frames. For example, the display may initially display images in a side-by-side configuration (e.g., 420, 422) displaying a SWEI image (e.g., image frame 416) and an SEI image (e.g., image frame 418). The user selects from the labels 440 or using the user interface 142 the overlaid configuration 424. The display circuit 198, using the 2D video processor circuit, may overlay the SWEI image over the SEI image (or vice versa) by aligning or registering the images with the ROI data acquisition location obtained by the position tracking circuit 148, forming the overlaid image 450. Optionally, the user may adjust the overlaid image 450 by adjusting a contrast or brightness of either the SWEI image or SEI image and/or a proportion of the SWEI image or the SEI image, respectively, forming the overlaid image 450.

The thumbnail configuration 426 displays a series of image frames from the one or more ultrasound imaging methods, such as SWEI or SEI. The thumbnail configuration 426 allows a user to view multiple image frames and select particular image frames to be viewed in another display layout (e.g., side-by-side configuration 420 and 422 or overlaid configuration 424). Optionally, the user may select image frames to be deleted from the memory 190 and/or the image memory 140.

Figure 5:
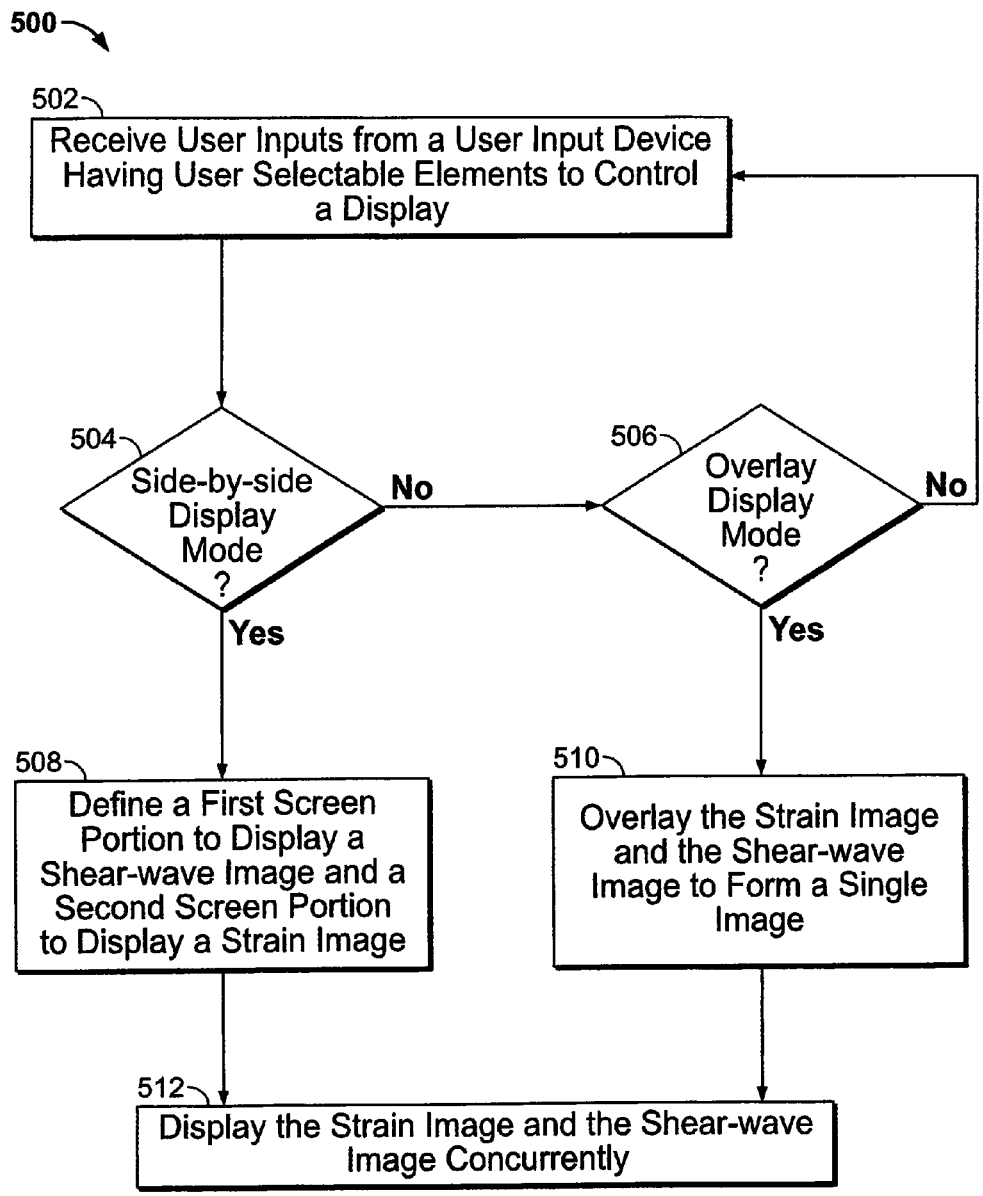
FIG. 5 is a flowchart of a method for displaying dual mode ultrasound images on a display in accordance with an embodiment.

FIG. 5 is a flowchart of a method 500 in accordance with various embodiments for displaying ultrasound images on the display 138 acquired using different modes of operation, such as the SWEI and the SEI. The method 500, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 500 may be able to be used as one or more algorithms to direct hardware to perform one or more operations described herein.

At 502, the method 500 includes receiving user inputs from a user input device having user selectable elements to control a display. For example, the user input device may be the user interface 142 described above. Alternatively, the user inputs may originate from the labels 440 viewed on the display 138.

At 504, the method 500 includes determining whether a side-by-side display mode was selected. For example, the display circuit 198 may receive from the user, using the user interface 142 and/or the labels 440, a display selection such as the side-by-side configuration 420 or 422 or the overlaid configuration 424. If the side-by-side display mode was selected, at 508, the method 500 defines a first screen portion to display the SWEI and a second screen portion to display the SEI. If the overlay display mode was selected, at 506, the method 500 overlays the SEI and the SWEI to form the single image 450 as described above. Once the display is configured to the selected display select, at 512, the method 500 includes displaying on the display 138 the SEI and the SWEI images concurrently.

Figure 6:
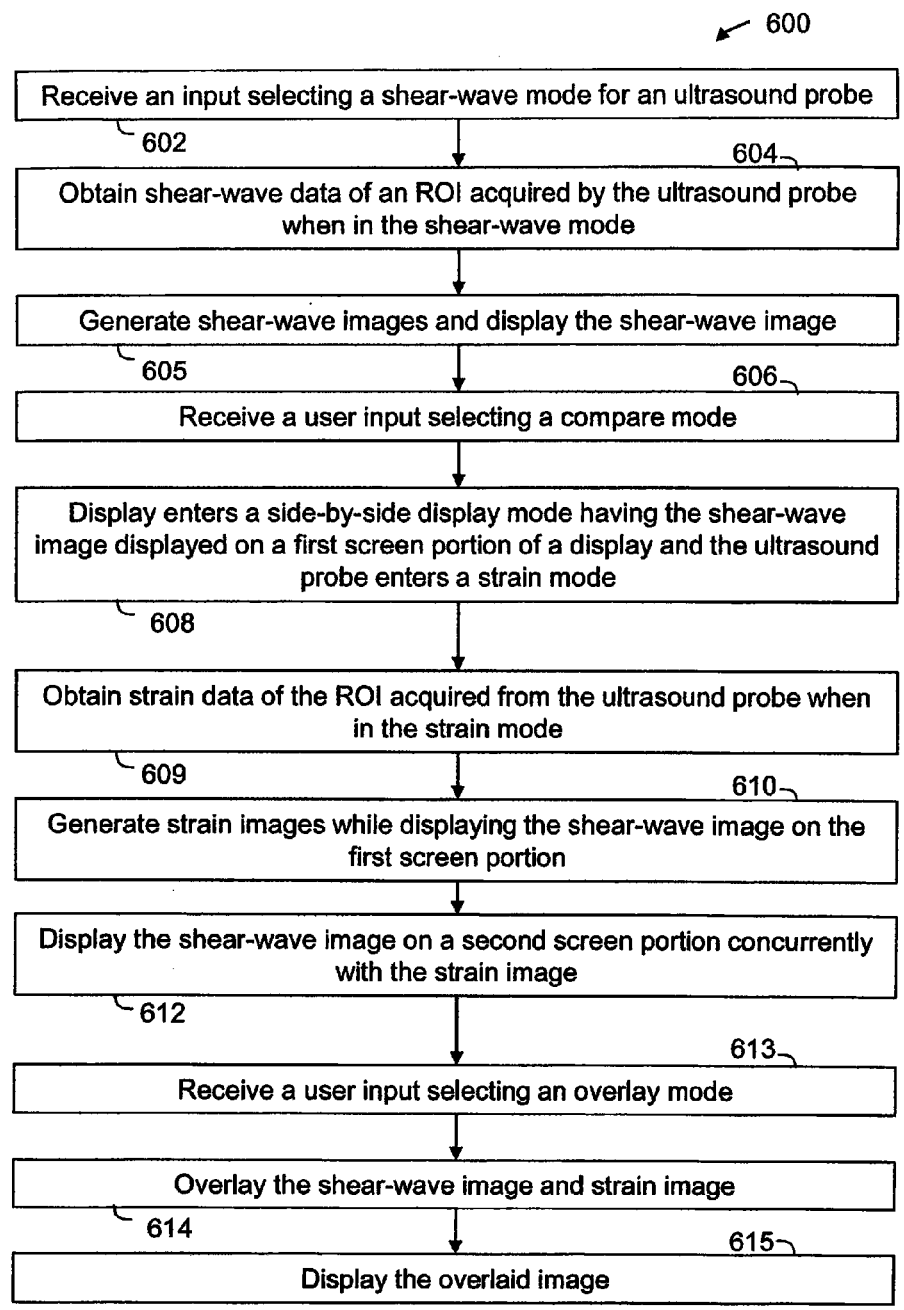
FIG. 6 is a flowchart of a method for displaying ultrasound images in accordance with an embodiment.

FIG. 6 is a flowchart of a method 600 in accordance with various embodiments for displaying ultrasound images. The method 600 for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 600 may be able to be used as one or more algorithms to direct hardware to perform one or more operations described herein. Additionally or alternatively, the method 600 may represent a work flow of a graphical user interface or operating system for acquiring and displaying, concurrently, one or more SWEI and SEI images.

At 602, the method 600 includes receiving an input selecting the shear-wave mode for the ultrasound probe 126. For example, the ultrasound imaging system 100 may receive a user input from the user interface 142. Optionally the user may be prompted by the display 138 of the ultrasound imaging system 100 to select a mode of the ultrasound probe 126 or to notify the imaging system 100 when the probe 126, the patient, and the user are ready to acquire shear-wave data following a predetermined workflow.

At 604, the method 600 includes obtaining shear-wave data of the ROI acquired by the ultrasound probe 126 when in the shear-wave mode and, at 605, generating shear-wave images and display the shear-wave image. For example, once the ultrasound imaging system 100 receives the input, such as from the user interface 142, the diagnostic circuit 136 may control the probe 126 to enter the shear-wave mode. Once the probe 126 is in the shear-wave mode, the probe 126 is configured or controlled by the shear-wave generating circuit to deliver a pushing pulse to generate a shear-wave within the ROI. After the shear-wave is generated, the probe 126 measures the echoes scattered from the ROI as the shear-wave passes through the ROI. The diagnostic circuit 136 receives the electrical signals from the probe 126. The elastography circuit 166 processes sets of vector data values, which correspond to shear-wave data from the electrical signals, where each set defines an individual SWEI frame. The shear-wave data may be stored on the memory 190 or on the memory 134 and/or the image memory 140. The scan converter circuit 192 accesses and obtains from the memory (e.g., 190, 134) the shear-wave data vector values associated with the SWEI images and converts the set of vector values to Cartesian coordinates to generate the SWEI images formatted for display. Once the SWEI image is processed by the display circuit 198 (as described above), the SWEI image is displayed on the display 138. Optionally, the scan converter circuit 192 may store the SWEI images on the memory 190 and/or the image memory 140. It should be noted that the scan converter circuit 192 may produce multiple series of SWEI images formatted for display based on the amount of shear-wave data stored on the memory (e.g., 190, 134).

At 606, the method 600 includes receiving a user input selecting a compare mode such that, at 607, the display 138 enters a side-by-side display mode (e.g., 420, 422) having the shear-wave image display on a first display portion (e.g., 416, 418) of the display 138 and the ultrasound probe 126 enters the strain mode. For example, the ultrasound system 100 may receive the user input from the user interface 142. The display 138 switches to the side-by-side configuration 422 such that the SWEI image is displayed at the image frame 416 (e.g., first display portion). The diagnostic circuit 136 may, due to the user input, operate the probe control or instruct the probe to enter into the strain mode. While in the strain mode, the strain circuit 125 controls or configures the probe 126 to generate a mechanical (e.g., surface vibration, freehand or step quasi-static surface displacement, or the like) or radiation force on the patient or ROI.

At 608, the method includes obtaining strain data of the ROI acquired by the probe 126 when in the strain mode. And at 610, the method further includes generating strain images while displaying the shear-wave image on the first display portion such that, at 612, display the shear-wave image and the strain image concurrently. For example, while the probe 126 generates the mechanical (e.g., surface vibration, freehand or step quasi-static surface displacement, or the like) or radiation force on the patient or ROI, the probe 126 measures the echoes scattered from the ROI before and after the ROI is compressed by the mechanical or radiation force. The diagnostic circuit 136 receives the electrical signals from the probe 126 and the elastography circuit 166 processes sets of vector data values corresponding to strain data from the electrical signals, where each set defines an individual SEI frame. The strain data may be stored on the memory 190 or on the memory 134 and/or the image memory 140. The scan converter circuit 192 accesses and obtains from the memory (e.g., 190, 134) the strain data vector values associated with the SEI images and converts the set of vector values to Cartesian coordinates to generate the SEI images formatted for the display portion of the display 138. Once the SEI image is processed by the display circuit 198 (as described above), such that the SEI image is displayed concurrently with the SWEI image having separate display portions of the display 138, respectively.

It should be noted, as mentioned above, that certain steps of the method may be performed in a different order than described above. For example, the ultrasound system 100 may receive strain data and generate strain images before the shear-wave data is acquired by the probe 126. Accordingly, in the compare mode, strain images generated by the strain data may be displayed in a display portion of the display 138 while the ultrasound probe 126 enters the shear-wave mode to acquire shear-wave data which is generated into shear-wave images displayed on the alternate display portion of the display 138.

At 610, the method includes receiving a user input selecting an overlay mode such that, at 614, overlay the shear-wave image and strain image, and at 615, displaying the overlaid image, for example, as described in the method 500 at 506.

Additionally or alternatively, the user may view the SWEI or SEI images while the probe 126 is obtaining measurement data while in the SEI or SWEI mode, respectively. For example, the user has acquired the SWEI data. The scan converter 192 accesses and obtains from the memory 190 the shear-wave data and generates the SWEI which is displayed on the display 138, after being processed by the display circuit 198. It should be noted that the SWEI may have been displayed while acquiring the SWEI data or once the acquisition of SWEI has been completed. The ultrasound imaging system 100 receives the user input to operate the probe 126 in a compare mode. The system switches to the side-by-side configuration 422 such that the SWEI is displayed at the image frame 416 and the image frame 418 displays a real-time SEI being measured from the probe 126 processed by the detection circuit 136. The user may pause the probe 126 from acquiring electrical signals corresponding to the strain data, such that the display 138 displays the most recent SEI image on the image frame 418. Optionally, the user may select the thumbnail configuration 426 which displays a series of SEI image captured during the strain mode and/or SEI image from previous strain mode measurements. While in the thumbnail configuration 426, the user may select, from the arrangement of thumbnail SEI image 460, a desired SEI. Once the user selects the desired SEI, the user may control the ultrasound imaging system 100, using the user interface 142, to display the overlaid configuration 424 with the SWEI image and the desired SEI. It should be noted that the SEI or strain data may be acquired before the SWEI or shear-wave data. Further it should be appreciated, that the user may select a desired SWEI image before acquiring the SEI data or after the desired SEI was selected.

Figure 7:
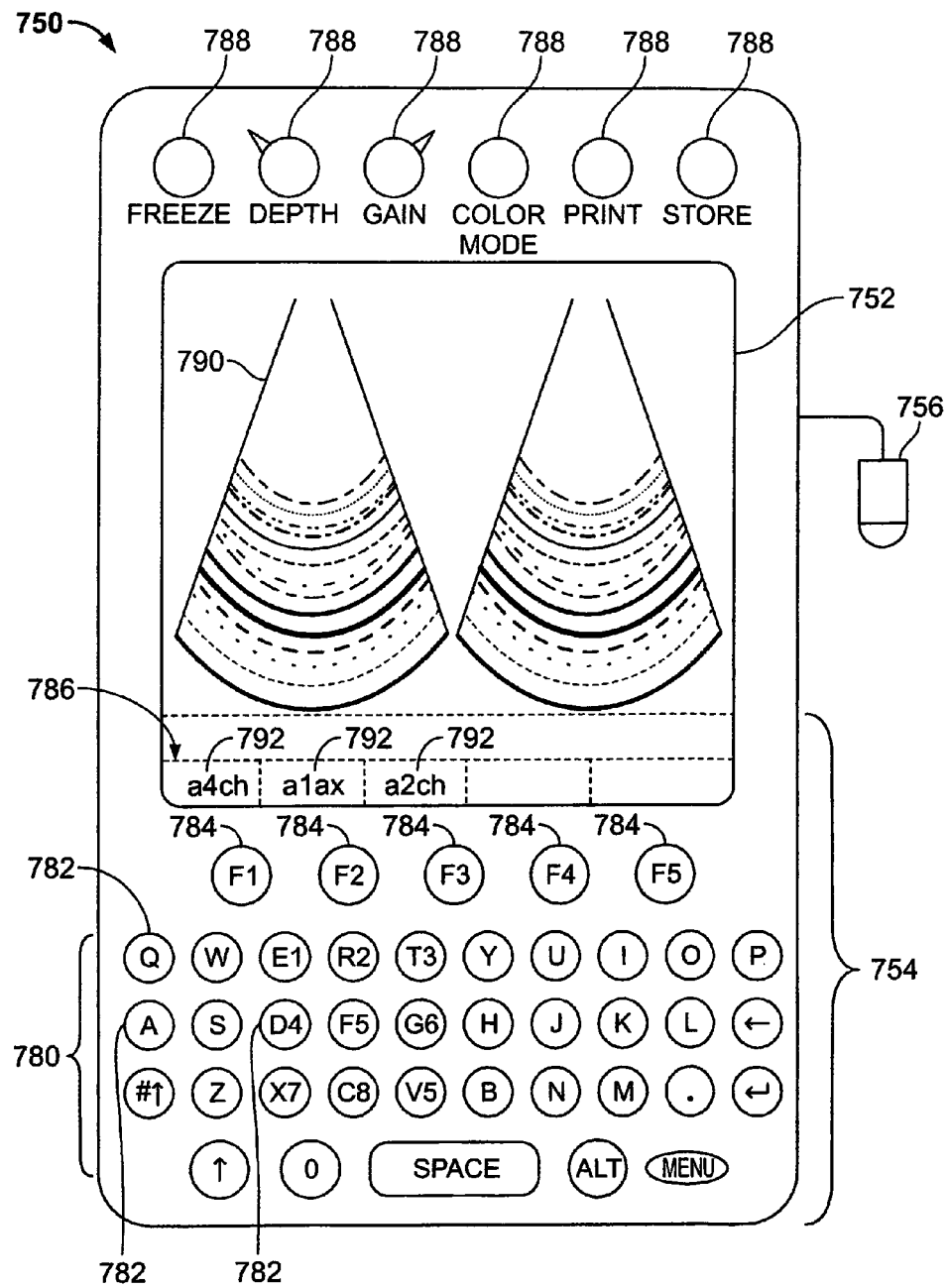
FIG. 7 is an illustration of a hand carried or pocket-sized ultrasound imaging system in accordance with an embodiment.
Figure 8:
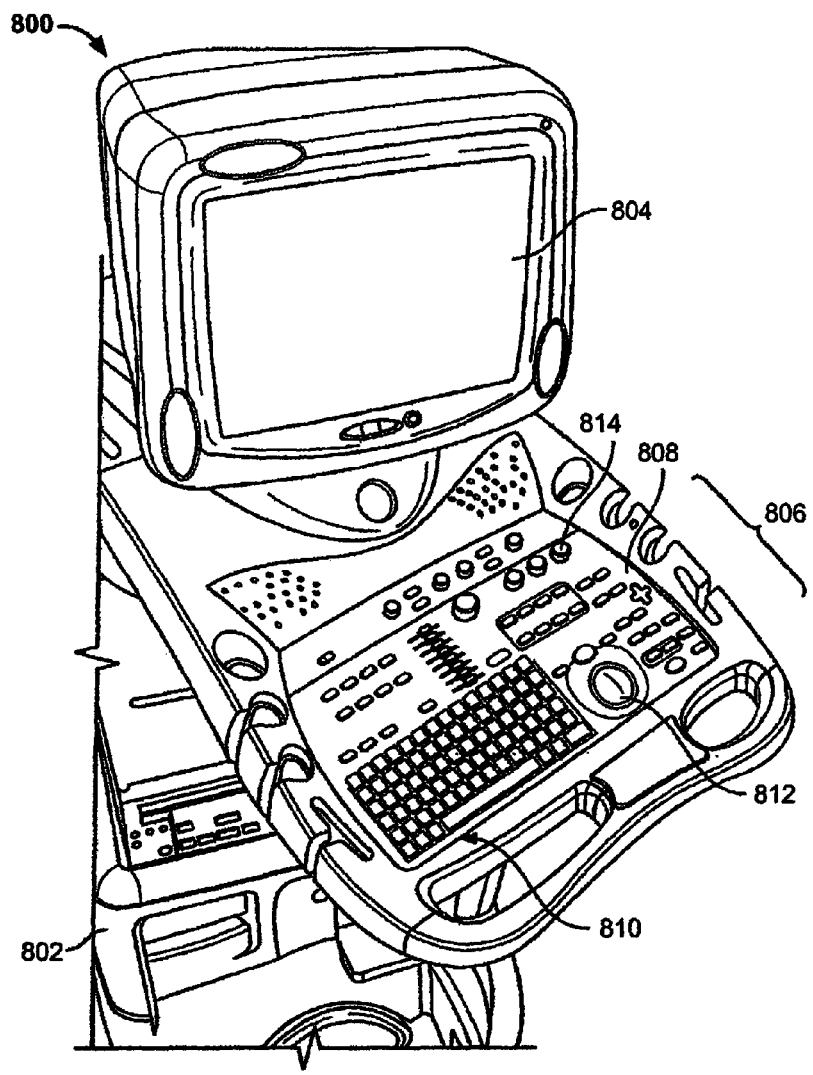
FIG. 8 is an illustration of a console-based ultrasound imaging system in accordance with an embodiment.
Figure 9:
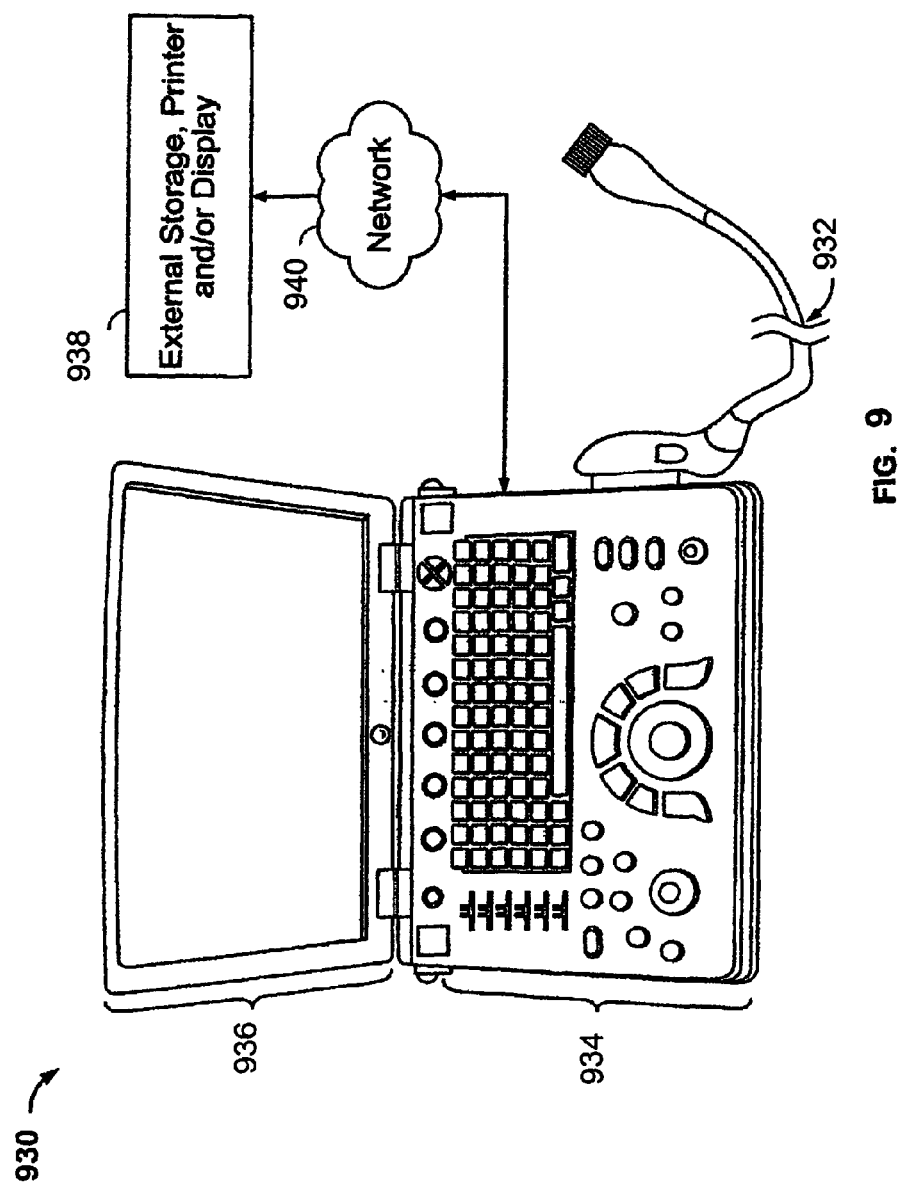
FIG. 9 is an illustration of a miniaturized ultrasound imaging system in accordance with an embodiment

The ultrasound system 120 of FIG. 2 may be embodied in a small-sized system, such as laptop computer or pocket-sized system as well as in a larger console-type system. FIGS. 7 and 9 illustrate small-sized systems, while FIG. 8 illustrates a larger system.

FIG. 7 illustrates a hand carried or pocket-sized ultrasound imaging system 750 wherein the display 752 and user interface 754 form a single unit. By way of example, the pocket-sized ultrasound imaging system 750 may be a pocket-sized or hand-sized ultrasound imaging system approximately 2 inches wide, approximately 4 inches in length, and approximately 0.5 inches in depth and weighs less than 3 ounces. The pocket-sized ultrasound imaging system 750 generally includes the display 752, user interface 754, which may or may not include a keyboard-type interface and an input/output (I/O) port for connection to a scanning device, for example, an ultrasound probe 756. The display 752 may be, for example, a 320×320 pixel color LCD display (on which a medical image 790 may be displayed). A typewriter-like keyboard 780 of buttons 782 may optionally be included in the user interface 754.

Multi-function controls 784 may each be assigned functions in accordance with the mode of system operation (e.g., displaying different views). Therefore, each of the multi-function controls 784 may be configured to provide a plurality of different actions. Label display areas 786 associated with the multi-function controls 784 may be included as necessary on the display 752. The system 750 may also have additional keys and/or controls 788 for special purpose functions, which may include, but are not limited to "freeze," "depth control," "gain control," "color-mode," "print," and "store."

One or more of the label display areas 786 may include labels 792 to indicate the view being displayed or allow a user to select a different view of the imaged object to display. The selection of different views also may be provided through the associated multi-function control 784. The display 752 may also have a textual display area 794 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 750 and the miniaturized ultrasound system 930 may provide the same scanning and processing functionality as the system 100.

FIG. 8 illustrates an ultrasound imaging system 800 provided on a movable base 802. The portable ultrasound imaging system 800 may also be referred to as a cart-based system. A display 804 and user interface 806 are provided and it should be understood that the display 804 may be separate or separable from the user interface 806. The user interface 806 may optionally be a touchscreen, allowing the operator to select options by touching displayed graphics, icons, and the like.

The user interface 806 also includes control buttons 808 that may be used to control the portable ultrasound imaging system 800 as desired or needed, and/or as typically provided. The user interface 806 provides multiple interface options that the user may physically manipulate to interact with ultrasound data and other data that may be displayed, as well as to input information and set and change scanning parameters and viewing angles, etc. For example, a keyboard 810, trackball 812 and/or multi-function controls 814 may be provided.

FIG. 9 illustrates a 3D-capable miniaturized ultrasound system 930 having a probe 932 that may be configured to acquire 3D ultrasonic data or multi-plane ultrasonic data. For example, the probe 932 may have a 2D array of elements as discussed previously with respect to the probe. A user interface 934 (that may also include an integrated display 936) is provided to receive commands from an operator. As used herein, "miniaturized" means that the ultrasound system 930 is a handheld or hand-carried device or is configured to be carried in a person's hand, pocket, briefcase-sized case, or backpack. For example, the ultrasound system 930 may be a hand-carried device having a size of a typical laptop computer. The ultrasound system 930 is easily portable by the operator. The integrated display 936 (e.g., an internal display) is configured to display, for example, one or more medical images.

The ultrasonic data may be sent to an external device 938 via a wired or wireless network 940 (or direct connection, for example, via a serial or parallel cable or USB port). In some embodiments, the external device 938 may be a computer or a workstation having a display. Alternatively, the external device 938 may be a separate external display or a printer capable of receiving image data from the hand carried ultrasound system 930 and of displaying or printing images that may have greater resolution than the integrated display 936.

It should be noted that the various embodiments may be implemented in hardware, software or a combination thereof. The various embodiments and/or components, for example, the circuits, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "circuit" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or circuits, a program circuit within a larger program or a portion of a program circuit. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A dual mode ultrasound imaging system comprising:
   an ultrasound probe configured to acquire shear-wave data during a shear-wave mode and strain data during a strain mode for a region of interest (ROI), wherein the shear-wave data is acquired at a different time relative to the strain data by the ultrasound probe;
   a diagnostic circuit configured to generate a shear-wave image and a strain image from the shear-wave data and the strain data, respectively; and
   a display concurrently displays the shear-wave image and the strain image.

2. The dual mode ultrasound imaging system of claim 1, further comprising a position tracking circuit configured to determine an ROI data acquisition location of the shear-wave data and the strain data, respectively, wherein the shear-wave image and the strain image are displayed in either a side-by-side configuration or overlaid to form a single displayed image, wherein the single displayed image is aligned using the ROI data acquisition location.

3. The dual mode ultrasound imaging system of claim 2, further comprising a user interface to adjust the single displayed image by increasing or decreasing at least one of a contrast, a brightness, or a proportion of the shear-wave data with respect to the strain data of the single displayed image.

4. The dual mode ultrasound imaging system of claim 2, further comprising a user interface to adjust the single displayed image by increasing or decreasing at least one of a contrast, a brightness, or a proportion of the strain data with respect to the shear-wave data of the single displayed image.

5. The dual mode ultrasound imaging system of claim 1, wherein the display is configured to display the shear-wave image when the strain data is being acquired or display the strain image when the shear-wave data is being acquired.

6. The dual mode ultrasound imaging system of claim 1, wherein the diagnostic circuit generates at least a second shear wave image or at least a second strain image when additional shear-wave data or strain data is acquired by the ultrasound probe, the display receives a user input that selects one of the shear-wave images and the strain images to display concurrently.

7. The dual mode ultrasound imaging system of claim 1, wherein a position tracking circuit receives location data from a plurality of position devices, wherein at least one position device is coupled to the ultrasound probe.

8. The dual mode ultrasound imaging system of claim 1, wherein a position tracking circuit determines the ROI data acquisition location based on a mechanical structure of the ROI.

9. A method for concurrently displaying ultrasound images, comprising:
   receiving an input selecting a shear-wave mode for an ultrasound probe;
   obtaining shear-wave data of a region of interest (ROI) acquired by the ultrasound probe when in the shear-wave mode;
   generating at least one shear-wave image from the shear-wave data and displaying the at least one shear-wave image on a display;
   receiving a user input selecting a compare mode;
   switching to a side-by-side display mode, wherein the at least one of the shear-wave images is displayed on a first display portion of the display;
   receiving an input selecting a strain mode for the ultrasound probe;
   obtaining strain data of the ROI acquired by the ultrasound probe when in the strain mode, wherein the shear-wave data is acquired at a different time relative to the strain data by the ultrasound probe;
   generating at least one shear-wave image from the strain data; and
   displaying the at least one strain image on a second display portion of the display concurrently with the at least one shear-wave image.

10. The method of claim 9, further comprising receive a user input selecting an overlay mode, wherein the at least one shear-wave image and the at least one strain image are overlaid to form a single displayed image.

11. The method of claim 10, further comprising using position tracking information with respect to the ultrasound probe to determine ROI data acquisition locations of the shear-wave data and strain data respectively, wherein the single displayed image is aligned at the ROI data acquisition locations, the position tracking information comprises location data outputted from a plurality of position devices, wherein at least one position device is coupled to the ultrasound probe.

12. The method of claim 9, further comprising receiving a user input to increase or decrease at least one of a contrast, a brightness, or a proportion of the at least one shear-wave image with respect to the at least one strain image when displayed concurrently.

13. The method of claim 9, further comprising receiving a user input to increase or decrease at least one of a contrast, a brightness, or a proportion of the strain image with respect to the shear-wave image when displayed concurrently.

14. The method of claim 9, further comprising receiving a user input selecting the at least one shear-wave image and the at least one strain image to display from a series of shear-wave images and strain images.

15. The method of claim 9, wherein a position tracking information is determined based on a mechanical structure of the region of interest (ROI).

16. The method of claim 9, wherein the ultrasound probe acquires the strain data before the shear-wave data.

17. The method of claim 9, wherein the ultrasound probe acquires the shear-wave data before the strain data.

18. A method for concurrently displaying dual mode ultrasound images on a display, comprising:
   receiving user inputs from a user input device having user selectable elements to control a display, wherein the user inputs control the display to enter a side-by-side display mode or an overlay display mode;
   defining, while the display is in the side-by-side display mode, a first screen portion to display a strain image and a second screen portion to display a shear-wave image, respectively, such that the strain image and the shear-wave image are displayed concurrently, wherein the shear-wave image is based on shear-wave data and the strain image is based on strain data, the shear-wave data being acquired at a different time relative to the strain data; and
   overlaying, while the display is in the overlay display mode, the strain image and the shear-wave image to form a single image, wherein the single image is aligned using region of interest (ROI) data acquisition locations of the strain image and the shear-wave image.

19. The method of claim 18, further comprising displaying a series of strain images or shear-wave images, wherein the user inputs select the strain image or shear-wave image from one of the images within the series of strain images or shear-wave images displayed, respectively.

20. The method of claim 18, further comprising receiving a user input to increase or decrease at least one of a contrast, a brightness, or a proportion of the strain image or shear-wave image.

* * * * *